US00PP20840P2

(12) United States Plant Patent
Larkman

(10) Patent No.: US PP20,840 P2
(45) Date of Patent: Mar. 16, 2010

(54) *LAVENDULA* PLANT NAMED 'LARKMAN BEE'

(50) Latin Name: *Lavendula hybrida*
Varietal Denomination: LARKMAN BEE

(76) Inventor: Clive Larkman, PO Box 567, Lilydale, Vic (AU) 3140

( * ) Notice: Subject to any disclaimer, the term of this patent is extended or adjusted under 35 U.S.C. 154(b) by 0 days.

(21) Appl. No.: 12/221,435

(22) Filed: Aug. 2, 2008

(51) Int. Cl.
*A01H 5/00* (2006.01)

(52) U.S. Cl. ..... Plt./445

(58) Field of Classification Search ..... Plt./445
See application file for complete search history.

*Primary Examiner*—Kent L Bell

(57) ABSTRACT

A new and distinct *Lavendula hybrida* cultivar named 'LARKMAN BEE' is disclosed, characterized by late Winter to early Spring flowering and moderate Fall reblooming. Flowers are distinctively blue-violet with larger terminal bracts. Plants are compact, with a slow to moderate growth habit. The new variety is a *Lavendula* hybrid, suitable to outdoor landscape and container use.

1 Drawing Sheet

Figure 1:
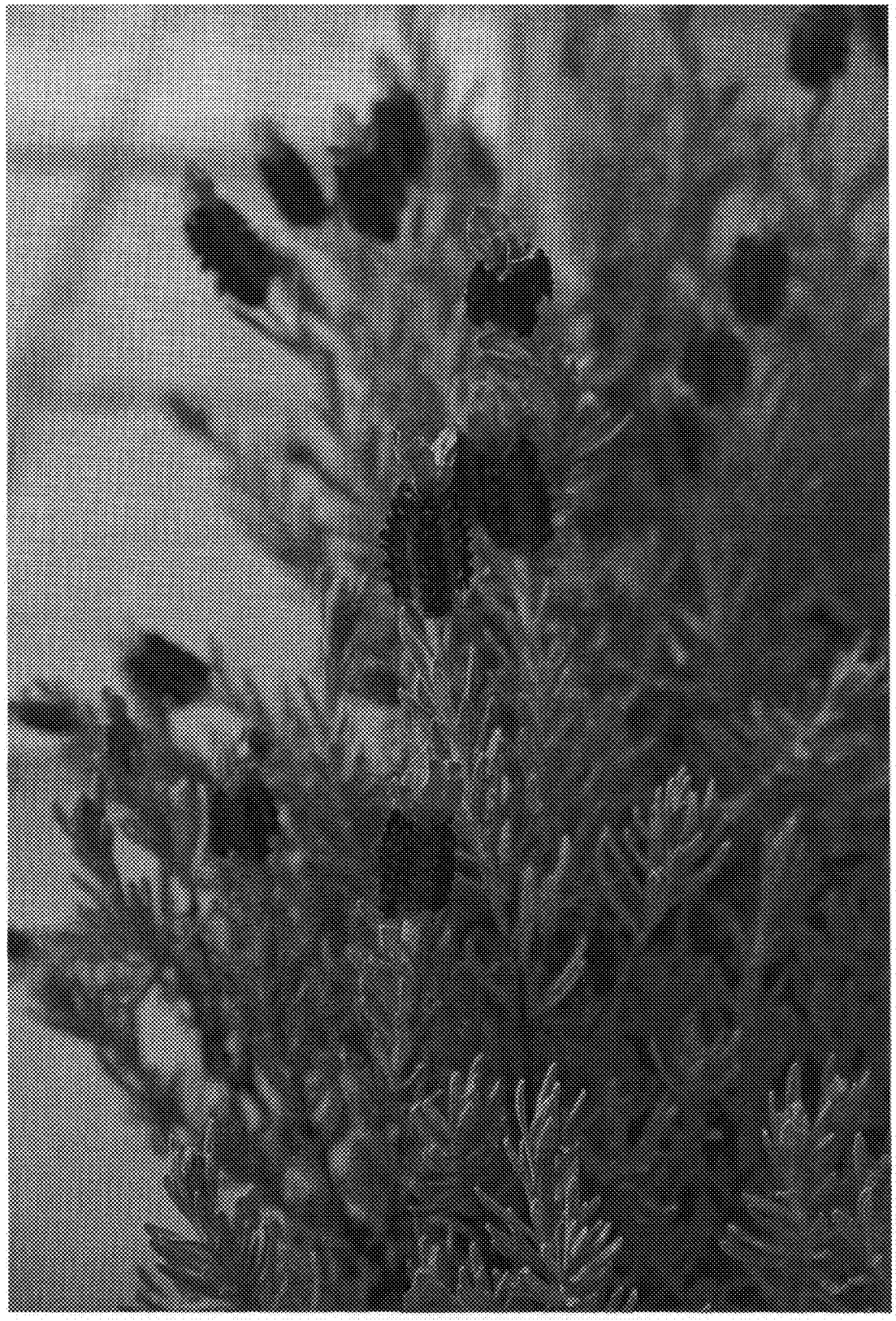

Latin name of the genus and species: *Lavendula hybrida.*
Varietal denomination: 'LARKMAN BEE'.

BACKGROUND OF THE INVENTION

The new cultivar is the product of a planned breeding program under the direction of the inventor, Clive Larkman, a citizen of the Australia. The objective of the breeding program was to produce *Lavendula* cultivars with large, high quality flowers. The seed parent is an unnamed, unpatented, plant of *Lavendula pedunculata*. The pollen parent is an unnamed plant of an unidentified *Lavendula* species. The new variety was discovered 1996, by the inventor in a group of seedlings resulting from that crossing, in Invercargill New Zealand.

Asexual reproduction of the new cultivar 'LARKMAN BEE' by vegetative cuttings was first performed in Invercargill New Zealand and has shown that the unique features of this cultivar are stable and reproduced true to type in successive generations.

SUMMARY OF THE INVENTION

The cultivar 'LARKMAN BEE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LARKMAN BEE' These characteristics in combination distinguish 'LARKMAN BEE' as a new and distinct *Lavendula* cultivar:

1. Blue-violet flowers.
2. Unusually early blooming in late winter.
3. Moderate Fall re-blooming.
4. Moderate to slow growth habit to 25 cm in height.
5. Compact plants, resisting breaking apart with age.

PARENT COMPARISON

Plants of the new cultivar 'LARKMAN BEE' are similar to plants of the seed parent, *Lavendula pedunculata* in most horticultural characteristics, however, plants of the new cultivar 'LARKMAN BEE' produce consistently dark colored flowers, whereas the parent variety produces flowers of inconsistent color. Additionally, the new variety produces flowers with more terminal bracts; 4 to 6 compared to 2 to 3 of the seed parent. The terminal bracts of the new variety are also typically much wavier in appearance than the seed parent. Plants of the new variety are more compact, with a less open center than plants of the seed parent.

BRIEF DESCRIPTION OF THE PHOTOGRAPH

The accompanying photograph in FIG. 1 illustrates in full color a close-up of typical floral bracts and leaves of 'LARKMAN BEE' grown outdoors in Southern California. Age of the plant is approximately 6 months. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'LARKMAN BEE' plants grown outdoors in Southern California from Fall to Spring. The growing temperature ranged from approximately 10 to 15° C. at night to 20 to 30° C. during the day. Measurements and numerical values represent averages of typical flowering types. No chemical or photoperiodic treatments were given.

Botanical classification: *Lavendula* hybrid cultivar 'LARKMAN BEE.'

PROPAGATION

Time to rooting: 20 days at approximately 20° C.
Root description: Fine, well branched.

PLANT

Growth habit: Upright, aromatic perennial.
Height: Approximately 25 cm.

Plant spread: Approximately 40 cm.
Growth rate: Moderate to slow.
Branching characteristics: Moderate branching.
Length of lateral branches: Approximately 15 cm.
Diameter of lateral branches: Approximately .3 cm.
Texture of lateral branches: Rough, developing a woody texture.
Internode length: Approximately 2 cm.
Strength of stem: Flexible and strong.
Color of lateral branches: Near RHS Grey-Brown 199A.
Aspect: Upright.
Number of leaves per lateral branch: Approximately 100.

FOLIAGE

Leaf:
- *Arrangement.*—Opposite, simple.
- *Average length.*—Approximately 2.7 cm.
- *Average width.*—Approximately .4 cm.
- *Shape of blade.*—Linear.
- *Apex.*—Murcronate.
- *Base.*—Cuneate.
- *Attachment.*—Sessile.
- *Margin.*—Entire.
- *Texture of top surface.*—Slightly pubescent.
- *Texture of bottom surface.*—Smooth.
- *Leaf internode length.*—Approximately .4 cm.
- *Color.*—Young foliage upper side: Near R.H.S. Green 136D. Young foliage under side: Near RHS Green 138C. Mature foliage upper side: Near RHS Green N138B. Mature foliage under side: Near RHS Green 139C.
- *Venation.*—Type: One very prominent mid-vein, with a fine network of much smaller veins. Venation color upper side: Near RHS Green N138C.
- *Venation color under side.*—Near RHS Green 139D.

Petiole: Not present.

FLOWER

Bloom period: Naturally blooming profusely February through mid-May. Moderate reblooming in the Fall.
Inflorescence:
- *Form.*—Small single flower in verticillasters arranged in spikes. 9 to 11 rows of flowers. Flowers have small bracts, and large showy terminal bracts. Florets: Corolla tube is 2-lipped. *Size individual flowers*: *Length*: Approximately .3 cm. *Diameter*: Approximately .2 cm. Depth: Approximately 2 cm.
- *Inflorescence size, excluding terminal bracts.*—Length: Approximately 2.4 cm. Width: Approximately 1.4 cm. Coloration of individual flowers and entire spikes, excluding terminal bracts: Immature: Near RHS Blue 99A. Mature: Near RHS Violet-Blue 96B. Fading: Near RHS Violet-Blue 96D.

Terminal bracts:
- *Length.*—Approximately 1.9 cm.
- *Width.*—Approximately 1.1 cm.
- *Aspect.*—Slightly undulating.
- *Duration on plant.*—Approximately 6 weeks, with good color. Persistent.
- *Shape.*—Obovate.
- *Apex.*—Acute, with irregular very shallow lobes.
- *Base.*—Rounded.
- *Margin.*—Entire.
- Duration on plant.—Approximately 6 weeks, with good color. Persistent.
- *Color.*—Upper side of immature bract: Near RHS Violet-Blue 96B. Under side of immature bract: Near RHS Violet-Blue 96B. Upper side of mature bract: Near RHS Violet-Blue 96C. Under side of mature bract: Near RHS Violet-Blue 96B.

Fragrance: Strong Lavender scent.
Peduncle:
- *Peduncle length.*—Approximately 1.5 cm.
- *Peduncle diameter.*—Approximately .2 cm.
- *Aspect.*—Upright.

Color: Near RHS Green N138D.

REPRODUCTIVE ORGANS

Androecium:
- *Stamens.*—2 to 4.
- *Anther shape.*—Linear.
- *Anther length.*—Approximately 0.05 cm.
- *Anther color.*—Near RHS Yellow 7A.
- *Pollen quantity.*—Minimal.

OTHER CHARACTERISTICS

Disease resistance: Neither resistance nor susceptibility to diseases or pests has been observed in this variety.
Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.
Fruit/seed production: Fruit and seed production not observed.

What is claimed is:

1. A new and distinct cultivar of *Lavendula* plant named 'LARKMAN BEE,' as herein illustrated and described.

* * * * *